United States Patent [19]

Drent et al.

[11] Patent Number: 4,861,912
[45] Date of Patent: Aug. 29, 1989

[54] PROCESS FOR THE PREPARATION OF A DIESTER OF ADIPIC ACID

[75] Inventors: Eit Drent; Johan Van Gogh, both of Amsterdam, Netherlands

[73] Assignee: Shell Oil Company, Houston, Tex.

[21] Appl. No.: 169,698

[22] Filed: Mar. 18, 1988

[30] Foreign Application Priority Data

Mar. 27, 1987 [GB] United Kingdom ................. 8707405

[51] Int. Cl.$^4$ ........................ C07C 67/38; C07C 51/14
[52] U.S. Cl. .................................... 560/204; 560/190; 560/191; 562/522
[58] Field of Search ...................... 560/190, 191, 204; 562/522

[56] References Cited

U.S. PATENT DOCUMENTS 4,256,909 3/1981 Kummer et al. ..................... 560/204
4,508,917 4/1985 Jenck ................................... 560/204
4,629,807 12/1986 Knifton ............................... 560/204

FOREIGN PATENT DOCUMENTS 0010581 2/1981 European Pat. Off. .
0092491 10/1983 European Pat. Off. .
0198521 10/1986 European Pat. Off. .

Primary Examiner—Werren B. Lone
Assistant Examiner—Vera C. Clarke

[57] ABSTRACT

Process for preparing adipic acid or esters thereof by:
(1) reacting 1,3-butadiene with CO and water or an alcohol with formation of pentenoic acid or esters thereof in the presence of a first carbonylation catalyst comprising a Pd compound and a polydentate ligand containing P, As or Sb,
(2) isolating pentenoic acid or esters thereof from the reaction mixture, and
(3) reacting the isolated pentenoic acid or esters with CO and water or an alcohol in the presence of a second carbonylation catalyst.

32 Claims, No Drawings

PROCESS FOR THE PREPARATION OF A DIESTER OF ADIPIC ACID

FIELD OF THE INVENTION

The invention relates to a process for the preparation of a compound of the general formula I

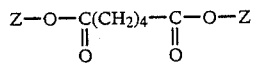   (I)

in which each Z represents a hydrogen atom or a hydrocarbon group.

BACKGROUND OF THE INVENTION

The commercially important dimethyl adipate, a compound of the general formula I, may be prepared, as described in U.S. Pat. No. 4,256,909, by the following steps: reacting 1,3-butadiene with carbon monoxide and methanol with formation of methyl pentenoate in the presence of a tertiary nitrogen base and a cobalt carbonyl catalyst; removing the greater part of the tertiary nitrogen base and excess hydrocarbons, and reacting the methyl pentenoate thus obtained with carbon monoxide and methanol in the presence of a cobalt carbonyl catalyst and the residual amount of tertiary nitrogen base to give dimethyl adipate.

A disadvantage of this known process is that step (a) requires the use of extremely high pressures, such as from 600 to 1200 bar.

It is an object of the present invention to avoid the use of extremely high pressures.

SUMMARY OF THE INVENTION

This invention relates a process for the preparation of a compound of the general formula I

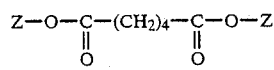   (I)

in which each Z represents a hydrogen atom or a hydrocarbon group, which process comprises:
(a) contacting 1,3-butadiene with carbon monoxide and a compound of the general formula II

ZOH (II)   (III)

in which Z represents a hydrogen atom or a hydrocarbon group, in the presence of a first carbonylation catalyst prepared by combining a palladium compound and a polydentate ligand having the general formula III

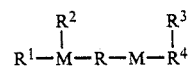   (III)

wherein each M represents an atom of Group VA of the Periodic Table of the Elements having an atom number in the range of from 15 to 51, R represents a divalent organic bridging group having in the range of from 2 to about 6 carbon atoms in the bridge, none of these carbon atoms carrying substituents that may cause steric hindrance, and $R^1$, $R^2$, $R^3$ and $R^4$ each represent a hydrocarbon group thereby forming a compound of the general formula IV

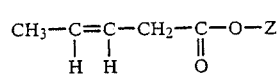   (IV)

in which Z represents a hydrogen atom or a hydrocarbon group;
(b) isolating the compound of the general formula IV from the reaction mixture obtained in (a), and
(c) reacting the compound isolated in (b) with carbon monoxide and a compound of the general formula II in the presence of a second carbonylation catalyst.

DESCRIPTION OF THE PREFERRED EMBODIMENTS

It has been found that step (a) of the process according to the present invention exhibits a high carbonylation rate and allows formation of compounds of the general formula IV with a very high selectivity, while applying relatively low pressures. The selectivity to a certain compound, expressed as a percentage, is defined as $100 \times a:b$ in which "a" is the amount of starting compound that has been converted into that certain compound and "b" is the total amount of starting compound that has been converted.

It has furthermore been found that the carbonylation rate in step (a) is very much enhanced while a high selectivity to compounds of the general formula IV is retained when a protonic acid having a $pK_a$ greater than 3, measured at 18° C. in aqueous solution, is also incorporated in the first carbonylation catalyst. Preferred such protonic acids are sterically hindered carboxylic acids. "Sterically hindered," as used herein, means that atoms or groups of atoms are present which interfere with one another, thus counteracting esterification of the carboxylic acid. Preferred sterically hindered carboxylic acids are sterically hindered benzoic acids such as, for example, 2,6-dimethylbenzoic acid, 2,6-diethylbenzoic acid, 2,4,6-trimethylbenzoic acid and 2,4,6-triethylbenzoic acid. Very good results have been obtained with 2,4,6-trimethylbenzoic acid. Further examples of protonic acids having a $pK_a$ greater than 3 are 3,4,5-trimethylbenzoic acid, m-hydroxybenzoic acid and p-hydroxybenzoic acid. Mixtures of protonic acids having a $pK_a$ greater than 3 may also be used.

Step (a) of the process according to the present invention may be carried out using a molar ratio protonic acid having a $pK_a$ greater than 3 to polydentate ligand having the general formula III which is not critical and may vary within wide limits. This molar ratio is preferably in the range of from 1.0 to 10, but the use of molar ratios below 1.0, for example between 0.1 and 1.0 and higher than 10, for example between 10 and 100, is not excluded.

In carrying out step (a) the following ratios are not critical and may vary within wide ranges, also above and below the preferred ranges stated hereinafter:
(a) the ratio gram-atom of palladium per mol of 1,3-butadiene, which ratio is preferably in the range of from $10^{-5}$ to $10^{-1}$;
(b) the ratio mol of polydentate ligand per gram-atom of palladium, which ratio is preferably in the range of from 1 to 10 and particularly of from 2 to 5; and
(c) the molar ratio compound of the general formula 11 to 1,3-butadiene, which ratio is preferably in the range of from 0.1 to 10.

Step (a) of the process according to the present invention may be carried out at a temperature and a pressure which are not critical and may vary within wide ranges. It is a feature of step (a) that even at relatively mild pressures very high carbonylation rates are observed. Step (a) is preferably carried out at a temperature in the range of from 50° C. to 200° C. and a pressure in the range of from to 100 bar. The use of temperatures between, for example, 20° C. and 50° C. or 200° C. and 225° C. and pressures between 10 and 25 bar or 100 and 150 bar, is not excluded.

According to a preferred embodiment of the present invention the second carbonylation catalyst is prepared by combining:

(a) palladium and/or a palladium compound,
(b) an acid having a $pK_a$ below 2.0, measured at 18° C. in aqueous solution, except hydrohalogenic and carboxylic acids, and
(c) a polydentate ligand having the general formula III in which R represents a divalent organic bridging group having in the range of from 3 to 6 carbon atoms in the bridge, said polydentate ligand being present in a molar ratio of acid having a $pK_a$ below 2.0 to polydentate ligand of greater than 0.5.

The polydentate ligand of the general formula III being used in step (a) preferably has in the range of from 3 to 6 carbon atoms, preferably 3 to 5 carbon atoms in the bridge of group R. The bridge in group R may contain hetero-atoms, for example oxygen atoms, but preferably exclusively consists of carbon atoms. The bridging group R may be part of a cyclic structure, for example an aromatic group, such as a phenylene group, or a cycloaliphatic group, such as a cyclohexylene group. The carbon to carbon bonds in the bridge are preferably saturated, but an ethylenically unsaturated carbon-carbon bond may be present.

The two atoms M in the general formula III may be different, but are preferably the same, and, more preferably, represent phosphorus atoms. However, the polydentate ligand may contain, for example, one phosphorus atom and one arsenic atom or two arsenic atoms or one phosphorus atom and one antimony atom.

In the polydentate ligands substituents offering steric hindrance should be absent, which means that no substituents are present that are able to hinder the formation of complex compounds having the general formula V

In formula V, R, $R^1$, $R^2$, $R^3$ and $R^4$ have the same meaning as in the general formula IV, $Y^-$ represents the anion of the palladium compound being used, while $Pd^{2+}$ can also be written as

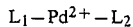

in which the ligands $L_1$ and $L_2$ are weakly coordinated solvent ligands, e.g. acetonitrile, methanol, acetone or acetylacetone, or correspond with those employed in the palladium compounds described hereinafter.

As used herein, the term "hydrocarbon groups" refers to hydrocarbon groups which can either be substituted or unsubstituted. The hydrocarbon groups represented by $R^1$, $R^2$, $R^3$ and $R^4$ may be unsubstituted or substituted with any substituents which do not interfere with the reaction. The hydrocarbon groups can be substituted or unsubstituted alkyl, substituted or unsubstituted cycloalkyl or substituted or unsubstituted aryl groups. The substituted or unsubstituted alkyl groups preferably have in the range of from 1 to 20 carbon atoms and, more preferably, in the range of from 2 to 6 carbon atoms. The substituted or unsubstituted cycloalkyl groups and substituted or unsubstituted aryl groups preferably have in the rage of from 6 to 14 carbon atoms. Particularly, $R^1$ and $R^3$ each represent a substituted or unsubstituted aryl group and $R^2$ and $R^4$ a substituted or unsubstituted alkyl or substituted or unsubstituted cycloalkyl group. Most preferably, $R^1$, $R^2$, $R^3$ and $R^4$ each represent a substituted or unsubstituted aryl group containing in the range of from 6 to 14 carbon atoms. The aryl groups may be, for example, naphthyl groups, but are preferably unsubstituted phenyl groups.

Examples of suitable substituents which may be present in $R^1$, $R^2$, $R^3$ and $R^4$ in formula IV are polar substituents such as chlorine and fluorine atoms; alkoxy groups having not more than five carbon atoms, preferably methoxy groups; trifluoromethyl groups, dibromomethyl groups and dimethylamino groups, and apolar substituents such as alkyl groups having not more than five carbon atoms, preferably methyl groups.

Preferred ligands of the general formula IV are 1,3-di(diphenylphosphino)propane and 1,4-di(diphenylphosphino)butane. Suitably, steps (a) and (c) are carried out with the same polydentate ligand of the general formula III.

Other examples of suitable ligands of the general formula IV are:
1,2-di(diphenylphosphino)ethane,
2,3-dimethyl-1,4-di(diphenylphosphino)butane,
1,4-di(dicyclohexylphosphino)butane,
1,3-di(di-p-tolylphosphino)propane,
1,4-di(di-p-methoxyphenylphosphino)butane,
2,3-di(diphenylphosphino)-2-butene,
1,3-di(diphenylphosphino)-2-oxopropane,
2-methyl-2-(methyldiphenylphosphine)-1,3-di(diphenylphosphino)propane,
o,o'-di(diphenylphosphino)biphenyl,
1,2-di(diphenylphosphino)benzene,
2,3-di(diphenylphosphino)naphthalene,
1,2-di(diphenylphosphino)cyclohexane,
2,2-dimethyl-4,5-di(diphenylphosphino)dioxolane,
1,5-di(diphenylphosphino)pentane,
1,6-di(diphenylphosphino)hexane,
tetrafluoro-1,2-di(diphenylphosphino)cyclobutene,
1,2-di[di(trifluoromethyl)phosphino]ethane,
1,3-di[di(trifluoromethyl)phosphino]propane,
1,3-di(phenyltrifluoromethylphosphino)propane,
hexafluoro-1,2-di(diphenylphosphino)cyclopentene,
octafluoro-1,2-(diphenylphosphino)cyclohexene, and

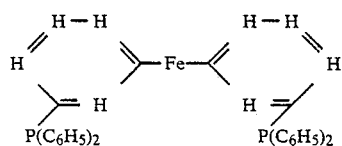

Mixtures of polydentate ligands may be used, for example of 1,3-di(diphenylphosphino)propane and 1,4-di(diphenylphosphino)butane.

It has, moreover, been found that the carbonylation rates in steps (a) and (b) are further enhanced when not only said polydentate ligands containing an element of Group VA are present, but also when one or more monodentate phosphine ligands are present. Preferred monodentate phosphine ligands are those having the general formula VI

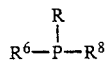
(VI)

in which $R^6$ represents a substituted or unsubstituted aryl group such as, for example, an anthryl or a naphthyl group, but preferably a phenyl group, and $R^7$ and $R^8$ each an alkyl group which can be either substituted or unsubstituted, preferably having in the range of from 1 to 20 carbon atoms, or a substituted or unsubstituted cycloalkyl group or a substituted or unsubstituted aryl group; the cycloalkyl groups preferably have in the range of from 3 to 7 and the aryl groups preferably have in the range of from 6 to 18 carbon atoms in the ring; $R^7$ and $R^8$ may represent together a substituted or unsubstituted alkylene or phosphacycloalkylene group. Mixtures of phosphines of the general formula VI may be present. Phosphines of the general formula VI may be present. Phosphines of the general formula VI in which each of $R^6$ and $R^7$ represents a substituted or unsubstituted phenyl group are preferred; particularly preferred in this group are phosphines in which also $R^8$ in the general formula VI represents a substituted or unsubstituted phenyl group.

The first carbonylation catalyst and the second carbonylation catalyst when prepared as described hereinbefore may be heterogeneous but are preferably homogeneous. Suitable palladium compounds for use in steps (a) and (c) are salts of palladium with, for example, nitric acid, sulfuric acid or carboxylic acids. Salts of hydrohalogenic acids can in principle be used as well, but they have the drawback that the halogen ion may produce corrosion. Palladium(II) salts of alkanoic acids having not more than 12 carbon atoms per molecule are preferred. Palladium(II) acetate is particularly preferred. Further, palladium complexes may be used, for example palladium acetylacetonate, o-tolylphosphinepalladium acetate and bis(triphenylphosphine)palladium sulphate. Palladium on carbon and palladium combined with an ion exchanger form suitable heterogeneous catalysts. Mixtures of palladium compounds may be used, for example of palladium(II) acetate and palladium acetylacetonate.

The acid having a $pK_a$ below 2.0 and used for the preparation of the second carbonylation catalyst preferably has a noncoordinating anion, by which is meant that little or no covalent interaction takes place between the palladium and the anion. Typical examples of such anions are $PF_6^-$, $SbF_6^-$, $BF_4^-$ and $ClO_4^-$.

Preferred acids are for example, sulfonic acids and acids that can be formed, possibly in situ, by interacting a Lewis acid such as, for example $BF_3$, $AsF_5$, $SbF_5$, $PF_5$, $TaF_5$ or $NbF_5$ with a Broensted acid such as, for example, a hydrohalogenic acid, in particular HF, fluorosulfonic acid, phosphoric acid or sulfuric acid. Specific examples of acids of the latter type are fluorosilicic acid, $HBF_3$, $HPF_6$ and $HSbF_6$. Examples of suitable sulfonic acids are fluorosulfonic acid and chlorosulfonic acid and the hereinafter specified sulfonic acids.

A preferred group of acids having a $pK_2$ below 2.0 has the general formula VII

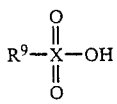
(VII)

wherein X represents a sulfur or a chlorine atom and, if X represents a chlorine atom, $R^9$ represents an oxygen atom and, if X represents a sulfur atom, $R^9$ represents an OH group or a hydrocarbon group which can either be substituted or unsubstituted.

When the hereinbefore stated acids are used in the process according to the invention, the anions of the acids can be considered to be non-coordinating.

In the acids having the general formula VII, the substituted or substituted hydrocarbon group represented by $R^9$, is preferably an alkyl, aryl, aralkyl or alkaryl group having 1-30, in particular 1-14, carbon atoms. The hydrocarbon group may, for example, be substituted with halogen atoms, in particular fluorine atoms.

Examples of suitable acids of the general formula VII are perchloric acid, sulfuric acid, 2-hydroxypropane-2-sulfonic acid, p-toluenesulfonic acid and trifluoromethanesulfonic acid, the last two acids being the most preferred. The acid of the general formula VII can also be an ion exchanger containing sulfonic acid groups, such as, for example, Amberlite 252 H ("Amberlite" is a trade name). In that case, the hydrocarbon group $R^9$ represents a polymeric hydrocarbon group substituted with sulfonic acid groups such as, for example, a polystyrene group.

In carrying out step (c) in the preferred manner described hereinbefore the following ratios are not critical and may vary within wide ranges, also above and below the preferred ranges stated hereinafter:
(a) the ratio gram-atom of palladium per mol of compound of the general formula IV, which ratio is preferably in the range of from $10^{-5}$ to $10^{-1}$;
(b) the ratio mol of polydentate ligand per gram-atom of palladium, which ratio is preferably in the range of from 1 to 10 and particularly of from 2 to 5; and
(c) the molar ratio compound of the general formula II to compound of the general formula IV, which ratio is preferably in the range of from 10:1 to 1:1.

Step (c) when carried out in the preferred manner described hereinbefore may be carried out at a temperature and a pressure which are not critical and may vary within wide ranges. It is a feature of step (c) that even at relatively mild pressures very high carbonylation rates are observed. Step (c) is preferably carried out at a temperature in the range of from 50° C. to 200° C. and a pressure in the range of from 25 to 100 bar. The use of temperatures between, for example, 20° C. and 50° C. or 200° C. and 225° C. and pressures between 10 and 25 bar or 100 and 150 bar, is not excluded. Steps (a) and (c) may suitably be carried out at the same temperature.

The reaction mixture formed in step (a) of the process according to the present invention contains compound of the general formula IV, unreacted 1,3-butadiene, unreacted compound of the general formula II and the first carbonylation catalyst. The compound of the general formula IV may be isolated from the reaction mixture obtained in step (a) in any desired manner. It is a feature of the present invention that the compound of the general formula IV can be isolated by means of distillation, yielding a fraction of unreacted 1,3-butadiene, a fraction of unreacted compound of the general formula II, a fraction of compound of the general formula IV and a residue containing the first carbonylation catalyst. It has been found that the first carbonylation catalyst contained in the residue is still active and may be used for the carbonylation of further quantities of 1,3-butadiene according to step (a) of the process according to the present invention. The unreacted 1,3-butadiene and the unreacted compound of the general formula II may, of course, also be re-used in step (a).

According to another preferred embodiment of the present invention the second carbonylation catalyst is prepared by combining a cobalt carbonyl and a tertiary amine. Suitably, the tertiary amine has a $pK_a$ in the range of from 3 to 11 and is preferably an N-heterocyclic tertiary amine. Particularly preferred are pyridine ($pK_a=5.3$), alkyl-substituted pyridines in which the alkyl groups have in the range of from 1 to 5 carbon atoms, alkoxy-substituted pyridines in which the alkoxy groups have in the range of from 1 to 5 carbon atoms and cycloalkyl-, cycloalkyloxy-, aryl- and aryloxysubstituted pyridines in which the cycloalkyl, cycloalkyloxy, aryl and aryloxy groups have in the range of from 6 to 14 and preferably 6 carbon atoms. Very good results have been obtained with 3,4-dimethylpyridine and 4-phenoxypyridine. Other examples of suitable tertiary amines are quinoline ($pK_a=4.9$), isoquinoline ($pK_2=5.4$), 2,2'-bipyridyl ($pK_a=4.1$), 2-picoline ($pK_a=5.2$), 3-picoline ($pK_a=6.0$), 4-picoline ($pK_a=6.0$), 2,3-dimethylpyridine ($pK_a=6.6$), 2,4-dimethylpyridine ($pK_a=7.0$), 3,5-dimethylpyridine ($pK_a=6.2$) and 4-benzylpyridine ($pK_a=5.2$). Further examples are trialkylamines, for example trimethylamine ($pK_a=9.8$) and triethylamine ($pK_a=11.0$) and dialkylarylamines, for example N,N-dimethylaniline ($pK_a32\ 5.2$) and N,N-diethylaniline ($pK_a=6.6$). It is preferred to use tertiary amines which have a higher boiling point than the pentenoic acid or esters being carbonylated, so that the latter can readily be distilled from the reaction mixture.

The cobalt carbonyl may be added as such to form the second carbonylation catalyst or may be formed in situ from a cobalt salt, for example cobalt acetate or cobalt formate. Suitably, the cobalt carbonyl is added as such, for example as dicobalt octacarbonyl or as a cobalt-carbonyl hydride.

In carrying out step (c) by using a second carbonylation catalyst prepared by combining a cobalt carbonyl and a tertiary amine, the following ratios are not critical and may vary within wide ranges, also above and below the preferred ranges stated hereinafter:

(a) the molar ratio cobalt carbonyl to compound of the general formula IV, which ratio is preferably in the range of from 1:50 to 1:1000;

(b) the molar ratio cobalt carbonyl to tertiary amine, which ratio is preferably in the range of from 1:1 to 1:100; and (c) the molar ratio compound of the general formula II to compound of the general formula IV, which ratio is preferably in the range of from 10:1 to 1:1.

Step (c), when carried out by using a second carbonylation catalyst prepared by combining a cobalt carbonyl and a tertiary amine, may be carried out at a temperature and a pressure which are not critical and may vary within wide ranges, preferably at a temperature in the range of from 120° C. to 200° C. and a pressure in the range of from 25 to 100 bar. The use of temperatures between, for example, 50° C. and 120° C. or 200° C. and 250° C. and pressures between 10 and 25 bar or 100 and 150 bar, is not excluded. In the presence of said cobalt-containing catalyst step (c) is preferably carried out in the presence of a small amount of hydrogen, for example, in an amount in the range of from 0.1 to 5% by volume, calculated on carbon monoxide, to enhance the rate of carbonylation.

The compound of the general formula I may be isolated from the reaction mixture obtained in step (c) in any desired manner, for example by means of distillation.

The carbon monoxide in steps (a) and (c) may be used pure or diluted with an inert gas, for example nitrogen, a noble gas or carbon dioxide. The presence of more than 5% by volume of hydrogen in step 1 is generally undesirable, because this may cause hydrogenation of 1,3-butadiene.

Steps (a) and (c) of the process according to the present invention may be carried out in the presence of one of the reactants as a solvent, for example of an alcohol of the general formula II. It may, however, be desired to carry out steps (a) and (c) in the presence of a separate solvent. Any inert solvent may in principle be used. Examples of suitable solvents are ketones, such as acetone, methyl ethyl ketone, methyl isobutyl ketone, acetophenone, cyclohexanone and acetylacetone; ethers such as anisole, 2,5,8-trioxanonane (also referred to as "diglyme"), diethyl ether, diphenyl ether and diisopropyl ether; aromatic hydrocarbons, such as benzene, toluene, the three xylenes and ethylbenzene; halogenated aromatic compounds, such as chlorobenzene and o-dichlorobenzene; halogenated alkanes, such as dichloromethane and carbontetrachloride; alkanes, such as hexane, heptane, octane and 2,2,3-trimethylpentane; cycloalkanes, such as cyclohexane and methylcyclohexane; nitriles, such as benzonitrile and acetonitrile; esters, such as methyl benzoate, methyl acetate and butyrolactone; sulfoxides, such as dimethyl sufoxide; sulfones, such as diisopropyl sulfone, tetrahydrothiophene-1,1-dioxide (also referred to as "sulfolane"), 2-methyl-4-butylsulfolane and 3-methylsulfolane. N-methylpyrrolidone is another example of a solvent. Mixtures of two or more solvents may be used. It has, furthermore, been found that carrying out step (a) in the presence of the pentenoic esters being prepared as a solvent further enhances the carbonylation rate and the selectivity to pentenoic esters.

Z in the compound of the general formula II preferably represents a hydrocarbon group. In this preferred case the compounds of the general formula I and IV are esters. Steps (a) and (c) may be carried out with different compounds of the general formula II but are preferably carried out with the same compound. The alcohol may be aliphatic, cycloaliphatic or aromatic. Aliphatic alcohols, particularly alkanols, are preferred. Among the alkanols those having not more than five, and particularly not more than four, carbon atoms per molecule are preferred. Examples of such alkanols are methanol, ethanol, propanol, 2-propanol, butanol, 2-butanol, tert-butyl alcohol and pentanol. Most preferred are methanol and ethanol.

If desired, water may be used as the only compound of the general formula II, producing 3-pentenoic acid in step (a) and adipic acid in step (c). It is not excluded to use a mixture of water and an alcohol as compounds of the general formula 11, producing a mixture of 3-pentenoic acid and 3-pentenoic ester in step 1 and a mixture of adipic acid, mono-ester of adipic acid and diester of adipic acid in step (c). It is also possible to use water as the only compound of the general formula II in step 1 and an alcohol as the only compound of the general formula II in step 3, producing a mono-ester of adipic acid in step 3. Alternatively, step 1 is carried out with an alcohol as the only compound of the general formula II and step 3 with water as the only compound of the general formula II, producing a monoester of adipic acid in step 3.

The following Examples further illustrate the invention and are not intended to be construed as limiting the invention.

EXAMPLE 1

Step (a)—Preparation of ethyl pentenoates

A 1 l Hastelloy C autoclave ("Hastelloy" is a trade mark) was charged with palladium (II) acetate (2 mmol), 1,4-di(diphenylphosphino)butane (8 mmol), 2,4,6-trimethylbenxzoic acid (15 mmol), diphenyl ether (40 mol) and ethanol (30 ml) and then closed. After having flushed the contents of the autoclave with carbon monoxide by pressurizing to 11 bar and depressurizing, the pressure was set at 11 bar and 1,3-butadiene(16 ml) was introduced via a pump. The pressure was raised to 41 bar by admitting of carbon monoxide and then the temperature was raised to 150° C., at which value the pressure became 60 bar. Then, 1,3-butadiene and ethanol were introduced into the autoclave at a rate of 50 mmol/h each, the autoclave being connected to a supply line for carbon monoxide having a pressure of 60 bar, carbon monoxide slipping into the autoclave via a valve.

No pressure increase was observed in the autoclave over a period of 49 run hours, the catalyst being active over this period. The feed rates of 1,3-butadiene and ethanol were then each increased to 100 mmol per h and maintained at this value over a period of 4 h. The pressure remained constant at 60 bar over this period. Then, the autoclave was cooled to ambient temperature and depressurized, giving 418.5 g of liquid product which contained 361 g of a mixture of ethyl pentenoates. As 1,3-butadiene has been introduced into the autoclave in an amount of 174.2 g, a yield of 87.5% of ethyl pentenoates was calculated. The mixture of ethyl pentenoates had a content of ethyl 3-pentenoate of about 90%.

Step (b)—Isolation

The liquid product obtained in step 1 was separated by distillation, yielding ethyl pentenoates having a purity of 98.5%, the remaining 1.5% consisting mainly of ethyl butenyl ethers. The bottom product of the distillation contained the palladium (II) acetate and 1,4-di(diphenylphosphine)butane introduced into the autoclave at the start of step 1.

Step (c)—Preparation of diethyl adipate

A 300 ml Hastelloy C autoclave was charged with dicobaltoctacarbonyl (1 mmol), 3,4-dimethylpyridine (12 mmol), ethanol (30 ml) and ethyl pentenoates (25 ml) prepared and isolated as described in steps 1 and 2, respectively. The autoclave was flushed with carbon monoxide, pressurized with carbon monoxide and then heated to a temperature of 170° C., at which temperature the partial pressure of carbon monoxide was 60 bar. After a reaction time of 5 h the autoclave was allowed to adopt ambient temperature and the contents were analyzed by means of gas-liquid chromatography. The conversion of ethyl pentenoates was 76%, with a selectivity to diethyl adipate of 82%.

EXAMPLE 2

The experiment described in step (c) of Example 1 was repeated with the difference that the temperature in step 3 was 160° C. instead of 170° C. The conversion of ethyl pentenoates was 62%, with a selectivity to diethyl adipate of 84%.

EXAMPLE 3

The experiment described in Example 2 was repeated with the difference that the partial pressure of carbon monoxide was 59 bar instead of 60 bar and that hydrogen having a partial pressure of 1 bar was also present. The conversion of ethyl pentenoates was 70%, with a selectivity to diethyl adipate of 83%.

Comparison of Examples 2 and 3 shows that the presence of hydrogen in step (c) enhances the conversion of ethyl pentenoates.

EXAMPLE 4

The experiment described in Example 2 was repeated with the difference that 3,4-pyridine (12 mmol) was replaced with 4-phenoxypyridine (12 mmol). The conversion of ethyl pentenoates was 66%, with a selectivity to diethyl adipate of 84%.

EXAMPLE 5

Step (a)—Preparation of ethyl pentenoates

A 1 l Hastelloy C autoclave was charged with palladium(II) acetate (2 mmol), 1,4-di(diphenylphosphino)butane (8 mmol), 2,4,6-trimethylbenzoic acid (15 mmol), ethyl pentenoates (40 ml) as produced and isolated in steps 1 and 2, respectively, of Example 1 and ethanol (30 ml). After having flushed the contents of the autoclave with carbon monoxide by pressurizing to 11 bar and depressurizing, the pressure was set at 11 bar and 1,3-butadiene (16 ml) was introduced via a pump. The pressure was raised to 41 bar by admitting carbon monoxide and then the temperature was raised to 150° C., at which value the pressure became 60 bar. Then, 1,3-butadiene and ethanol was introduced into the autoclave at a rate of 50 mmol/h each, the autoclave being connected to a supply line for carbon monoxide having a pressure of 60 bar, carbon monoxide slipping into the autoclave via a valve.

No pressure increase was observed in the autoclave over a period of 54 run hours, the catalyst being active over this period. At the end of this period, when 237 ml of 1,3-butadiene had been added, the autoclave was allowed to adopt ambient temperature and depressurized, giving 354 g of liquid product which contained 308 g of a mixture of ethyl pentenoates, excluding the 40 ml introduced at the start of the experiment.

Step (b)—Isolation

The liquid product obtained in step 1 was separated by distillation, yielding ethyl pentenoates having a purity of 98.5%. The mixture of ethyl pentenoates had a content of ethyl 3-pentenoate of about 90%. The yield of ethyl pentenoates was 88%, calculated on the amount of 1,3-butadiene introduced into the autoclave.

Step (c)—Preparation of diethyl adipate

A 250 ml magnetically stirred Hastelloy C autoclave was charged with ethyl pentenoates (10 ml) prepared as described in steps 1 and 2, anisole (30 ml), palladium(II) acetate (0.4 mmol), 1,4-di(diphenylphosphino)butane (1.6 mmol) and p-toluenesulfonic acid (4 mmol). The autoclave was flushed with carbon monoxide, filled with carbon monoxide at a pressure of 40 bar, sealed and heated to a temperature of 155° C.

The conversion of ethyl pentenoates was 100%, the reaction rate was 150 mol of ethyl pentenoates per mol of palladium per h and the content of diethyl adipate in the diesters obtained was 70%.

We claim:

1. A process for the preparation of a compound of formula I $$Z-O-\underset{\underset{O}{\|}}{C}(CH_2)_4-\underset{\underset{O}{\|}}{C}-O-Z \quad (I)$$

wherein each Z represents a hydrogen atom or a hydrocarbon group, which process comprises:
  (a) contacting 1,3-butadiene with carbon monoxide and a compound of formula II $$ZOH \quad (II)$$

in which Z represents a hydrogen atom or a hydrocarbon group, in the presence of a first carbonylation catalyst prepared by combining a palladium compound and a polydentate ligand having formula III $$R^1-\underset{\underset{R^2}{|}}{M}-R-\underset{\underset{R^4}{|}}{M}-R^3 \quad (III)$$

wherein each M represents an atom of Group VA of the Periodic Table of the Elements having an atom number in the range of from 15 to 51, R represents a divalent organic bridging group having in the range of from 2 to about 6 carbon atoms in the bridge, none of these carbon atoms carrying substituents that may cause steric hindrance, and $R^1$, $R^2$, $R^3$ and $R^4$ each represent hydrocarbon group, thereby forming a compound of formula IV $$CH_3-\underset{\underset{H}{|}}{C}=\underset{\underset{H}{|}}{C}-CH_2-\underset{\underset{O}{\|}}{C}-O-Z \quad (IV)$$

in which Z represents a hydrogen atom or a hydrocarbon group;
  (b) isolating the compound of formula IV from the reaction mixture obtained in (a), and
  (c) reacting the compound isolated in (b) with carbon monoxide and a compound of formula II in the presence of a second carbonylation catalyst.

2. The process of claim 1 wherein each M in the general formula III represents a phosphorus atom.

3. The process of claim 1 wherein a protonic acid having a $pK_a$ greater than about 3, measured at 18° C. in aqueous solution, is incorporated in the first carbonylation catalyst.

4. The process of claim 3 wherein protonic acid having a $pK_a$ greater than about 3 is a sterically hindered carboxylic acid.

5. The process of claim 4 wherein the sterically hindered carboxylic acid is a sterically hindered benzoic acid.

6. The process of claim 3 wherein a molar ratio protonic acid having a $pK_a$ greater than about 3 to polydentate ligand having formula III in the range of from 1.0 to 10 is used in (a).

7. The process of claim 1 wherein (a) is carried out with a ratio gram-atom of palladium per mol of 1,3-butadiene, in the range of from about $10^{-5}$ to about $10^{-1}$, a ratio mol of polydentate ligand per gram-atom of palladium in the range of from about 1 to about 10 and a molar ratio compound of formula II to 1,3-butadiene in the range of from about 0.1 to about 10.

8. The process of claim 7 wherein said process is carried out at a temperature in the range of from about 50° C. to 200° C. and a partial pressure of carbon monoxide in the range of from about 25 to about 100 bar.

9. The process of claim 1 wherein the second carbonylation catalyst is prepared by combining:
  (a) palladium and/or a palladium compound,
  (b) an acid having a $pK_a$ below about 2.0, measured at 18° C. in aqueous solution, except hydrohalogenic and carboxylic acids, and
  (c) a polydentate ligand having formula III in which R represents a divalent organic bridging group having in the range of from 3 to 6 carbon atoms in the bridge.

10. The process of claim 9 wherein a molar ratio of acid having a $pK_a$ below about 2.0 to polydentate ligand greater than about 0.5 is used.

11. The process of claim 1 wherein the polydentate ligand present in (a) has in the range of from about 3 to about 6 carbon atoms in the bridge of group R.

12. The process of claim 1 wherein the bridge in group R in formula III exclusively consists of carbon atoms.

13. The process of claim 1 wherein $R^1$, $R^2$, $R^3$ and $R^4$ in formula III each represent an aryl group having in the range of from 6 to about 14 carbon atoms.

14. The process of claim 13 wherein $R^1$, $R^2$, $R^3$ and $R^4$ each represent a phenyl group.

15. The process of claim 12 wherein the polydentate ligand of formula III is 1,3-di(diphenylphosphino)propane or 1,4-di(diphenylphosphino)butane.

16. The process of claim 1 wherein said palladium compound is palladium acetate.

17. The process of claim 9 wherein said palladium compound is palladium acetate.

18. The process of claim 9 wherein the acid having a $pK_a$ below about 2.0 is an acid (a) that can be formed by interaction of a Lewis acid with a Broensted acid or (b) having formula VII $$R^9-\underset{\underset{O}{\|}}{\overset{\overset{O}{\|}}{X}}-OH \quad (VII)$$

in which X represents a sulfur or a chlorine atom and, if X represents a chlorine atom, $R^9$ represents an oxygen atom and, if X represents a sulfur atom, $R^9$ represents an OH group or a hydrocarbon group.

19. The process of claim 18 wherein the hydrocarbon group represented by $R^9$ is selected from the group consisting of an alkyl, aryl, aralkyl or alkaryl group having in the range of from 1 to about 30 carbon atoms.

20. The process of claim 19 wherein the acid is selected from the group consisting of p-toluenesulfonic acid and trifluoromethanesulfonic acid.

21. The process of claim 1 wherein (c) is carried out with a ratio gram-atom of palladium per mol of compound of formula IV in the range of from about $10^{-5}$ to abut $10^{-1}$, a ratio mol of polydentate ligand per gram-atom of palladium in the range of from about 1 to about 10 and a molar ratio compound of formula II to compound of the general formula IV in the range of from about 10:1 to about 1:1.

22. The process of claim 21 wherein said process is carried out at a temperature in the range of from about 50° C. to about 200° C. and a partial pressure of carbon monoxide in the range of from about 25 to about 100 bar.

23. The process of claim 1 wherein the reaction mixture obtained in (c) is separated by means of distillation into a distillate fraction containing the compound of the general formula I and a residual fraction containing the second carbonylation catalyst, which catalyst is recycled to (c) for re-use.

24. The process of claim 1 wherein the second carbonylation catalyst is prepared by combining a cobalt carbonyl and a tertiary amine.

25. The process of claim 24 wherein the tertiary amine is N-heterocyclic.

26. The process of claim 21 wherein the N-heterocyclic tertiary amine is selected from the group consisting of pyridine, an alkyl- or alkoxy-substituted pyridine in which the alkyl or alkoxy groups have in the range of from 1 to about 5 carbon atoms, and a cycloalkyl-, cycloalkyloxy-, aryl- or aryloxy-substituted pyridine in which the cycloalkyl, cycloalkoxy, aryl or aryloxy groups have in the range of from 6 to about 14 carbon atoms.

27. The process of claim 26 wherein the tertiary amine is selected from the group consisting of 3,4-dimethylpyridine and 4-phenoxypyridine.

28. The process of claim 24 wherein(c) is carried out with a molar ratio cobalt carbonyl to compound of formula IV in the range of from about 1:50 to about 1:1000, a molar ratio cobalt carbonyl to tertiary amine in the range of from about 1:1 to about 1:100 and a molar ratio compound of formula III to compound of formula IV in the range of from about 10:1 to 1:1.

29. The process of claim 28 wherein said process is carried out at a temperature in the range of from about 120° C. to about 200° C. and a pressure in the range of from about 25 to about 100 bar.

30. The process of claim 1 wherein Z in the general formula I represents an alkyl group having in the range of from 1 to about 5 carbon atoms.

31. The process of claim 30 wherein Z represents a methyl or an ethyl group.

32. The process of claim 1 wherein (b) is carried out by means of distillation into a distillate fraction containing the compound of formula IV and a residual fraction containing the first carbonylation catalyst which catalyst is recycled to (a) for re-use.

* * * * *